US007435843B2

(12) United States Patent
Chen et al.

(10) Patent No.: US 7,435,843 B2
(45) Date of Patent: *Oct. 14, 2008

(54) SYNTHESIS OF TAXOL ENHANCERS

(75) Inventors: Shoujun Chen, Billerica, MA (US);
Lijun Sun, Harvard, MA (US);
Zhi-Qiang Xia, Dedham, MA (US);
Keizo Koya, Brookline, MA (US);
Mitsunori Ono, Lexington, MA (US)

(73) Assignee: Synta Pharmaceuticals Corp.,
Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/440,429

(22) Filed: May 24, 2006

(65) Prior Publication Data

US 2006/0281811 A1    Dec. 14, 2006

Related U.S. Application Data

(63) Continuation of application No. 10/807,919, filed on Mar. 24, 2004, now Pat. No. 7,074,952, which is a continuation of application No. 10/193,076, filed on Jul. 10, 2002, now Pat. No. 6,825,235.

(60) Provisional application No. 60/304,318, filed on Jul. 10, 2001.

(51) Int. Cl.
*C07C 327/56* (2006.01)

(52) U.S. Cl. ........................................ 560/16; 560/147

(58) Field of Classification Search ................... 560/16, 560/147
See application file for complete search history.

(56) References Cited

U.S. PATENT DOCUMENTS

| 4,826,866 | A | 5/1989 | Taylor et al. |
| 5,300,278 | A | 4/1994 | Pasqualini et al. |
| 5,753,200 | A | 5/1998 | Zolotoochin et al. |
| 5,843,400 | A | 12/1998 | Fujibayashi et al. |
| 6,013,836 | A | 1/2000 | Hsu et al. |
| 6,172,108 | B1 | 1/2001 | Vega et al. |
| 6,172,188 | B1 | 1/2001 | Thastrup et al. |
| 6,235,787 | B1 | 5/2001 | Broadhurst et al. |
| 6,365,745 | B1 | 4/2002 | Matsui et al. |
| 6,399,659 | B2 | 6/2002 | Usui et al. |
| 6,656,971 | B2 | 12/2003 | Wu et al. |
| 6,762,204 | B2 | 7/2004 | Koya et al. |
| 6,800,660 | B2 | 10/2004 | Koya et al. |
| 6,825,235 | B2 | 11/2004 | Chen et al. |
| 6,897,335 | B2 | 5/2005 | Okabe et al. |
| 7,074,952 | B2 * | 7/2006 | Chen et al. .................. 560/174 |

FOREIGN PATENT DOCUMENTS

CH        482394 A      12/1969

OTHER PUBLICATIONS

Sun et al., Shengwu Huaxue Yu Shengwu Wuli Xuebao, 4(5), 539-550, 1964.*
Greene, T. W. et al., "Protection For The Carboxyl Group," *Protective Groups in Organic Synthesis*, Third Edition, 5, pp. 369-453.
Greene, T. W. et al., "Protection For The Amino Group," *Protective Groups in Organic Synthesis*, Third Edition, 7, pp. 494-653.
Henderson, N. D. et al., "Synthesis of new bifunctional compounds which selectively alkylate guanines in DNA, " *Anti-Cancer Drug Design*, 13:749-768 (1998).
Metzner, P. et al., "Sulfur Reagents in Organic Synthesis," *Best Synthetic Methods*, pp. 30-185.
"Activating Agents and Protecting Groups," *Handbook of Reagents for Organic Synthesis*, pp. 133-135.
Tsuji, T., et al., "Synthesis and Reactions of N-Aminothiouracils and Thiadiazolo [3,2-α] pyrimidinones," *Chem. Pharm. Bull.* 26(9):2765-2767 (1978).

(Continued)

*Primary Examiner*—Fiona T Powers
(74) *Attorney, Agent, or Firm*—Hamilton, Brook, Smith & Reynolds, P.C.

(57) ABSTRACT

Disclosed is a method of preparing a thiohydrazide product compound from a hydrazide starting compound. The hydrazide starting compound is represented by Structural Formula (I):

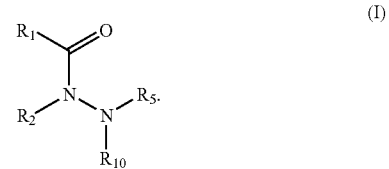

(I)

The thiohydrazide product compound is represented by Structural Formula (II):

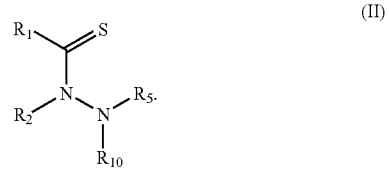

(II)

In Structural Formulas (I)-(II), $R_1$ and $R_2$ are independently an aliphatic group, a substituted aliphatic group, an aryl group or a substituted aryl group, or $R_1$ and $R_2$ taken together with the carbon and nitrogen atoms to which they are bonded, form a non-aromatic heterocyclic ring optionally fused to an aromatic ring. When $R_2$ is an aryl group or a substituted aryl group, then $R_5$ is a hydrazine protecting group; and when $R_2$ is an aliphatic or substituted aliphatic group, then $R_5$ is —H or a hydrazine protecting group. $R_{10}$ is —H or a substituted or unsubstituted alkyl group. The method comprising the step of reacting the starting compound with a thionylating reagent.

4 Claims, No Drawings

OTHER PUBLICATIONS

Przheval, N. M., et al., "A New General Synthesis of Bistetrafluoroborates of 2,3,4,5- Tetrasubstituted 1,3,4-Thiadiazoliums," *Synthesis* 5:463-464 (1993).

Badawy, M. A., "Synthesis and Reactions of 1,2,4-Triazino-1,2,4-Triazines," *Sulfur Letters* 11(1+2):21-28 (1990).

Mohamed, M. M., et al., "Synthesis & Some Reactions of 2-(α/β-Naphthyl)-3,1-benzoxazin-4(*H*)-ones 3-Amino-2-(β-naphthyl)quinazolin-4(3*H*)-one," *Indian Journal of Chemistry* 25B(2):207-211 (1986).

Barta-Szalai, G., et al., "Electron Deficient Heteroaromatic Ammonioamidates. XVII. N-(3-Quinazolinio)amidates. VI. The Photochemistry of N-(3-Quinazolinio)amidates in the Presence of α-Toluenethiol," *Acta Chemica Scandinavica B* 33:79-85 (1979).

Ueda, H. and Ohta, M., "Studies on Sulfur-Containing Heterocyclic Compounds," *Nippon Kagaku Zasshi*, 80:571-574 (1959).

Molina, P., et al., "Preparation of a Novel Type of Ligands Incorporating Two or Three 1,3,4-Thiadiazole Units," *Heterocycles* 36(6):1263-1278 (1993).

Molina, P., et al., "Methyl 2-Methyldithiocarbazate in Heterocyclic Synthesis: Preparation of 2,5-Disubstituted 1,3,4-Thiadiazoles, Bis(1,3,4-Thiadiazolium) Salts and Macrocycles containing 1,3,4-Thiadiazole Subunits, X-Ray Crystal Structure of 2,2'-Bis[4,5-dihydro-5-(2-hydroxyethylimino)-4-methyl-1,3,4-thiadiazole]," *J. Chem. Soc. Perkin Trans. 1 s* 5:1159-1166 (1991).

Branch, C. L., et al., "Synthesis of 6-Hydroxy-2-Methyl-3-Thioxo-2H-1,2,4-Triazin-5-one," *Synthetic Communications* 26(11):2075-2084 (1996).

Schwarz, J. and Just, H., "Virustatic Thiosemicarbazides," CA77:48081 (1972).

Rupp, W., "5-Amino-1,3,4-Thiadiazole Compounds," CA76:126992 (1972).

Baker, W., et al., "663: 1 : 4-*Diaryl*-1: 4-*dihydro*-1 : 2 : 4 : 5-*tetrazines and Derived Substances*," *Journal of The Chemical Society*, 3389-3394 (1950).

Jensen, K. A., et al., "Thiohydrazides and Thiohydrazones: A New Class of Antibacterial Substances," *Acta Chemica Scandinavica*, 6(Pt.II): 957-958 (1952).

Sato, T., et al., "Studies in Organic Sulfur Compounds. I. Thioformyl Phenylhydrazide, " *Bulletin of the Chemical Society of Japan*, 27(9):624-627 (1954).

Walter, W., et al., "Chapter 9: The Chemistry of the Thiohydrazide Group," *The Chemistry of Amides* (Ed. J. Zabicky), (London: Interscience Publishers), pp. 477-514 (1970).

El-Barbary, A.A., et al., "Studies in Organophosphorus Compounds, " *Tetrahedron* 36:3309-3315 (1980).

Heindel, N.D., et al., "Thiohydrazides and Acetylene Esters, A New Route to 1,3,4-Thiadiazoles," *Journal of Heterocyclic Chemistry*, 17(1): 191-193 (1980).

Cava, M.P., et al., "Thionation Reactions of Lawesson's Reagents, " *Tetrahedron*, 14(22): 5061-5087 (1985).

\* cited by examiner

SYNTHESIS OF TAXOL ENHANCERS

RELATED APPLICATIONS

This application is a continuation of U.S. patent application Ser. No. 10/807,919, filed Mar. 24, 2004, now U.S. Pat. No. 7,074,952 which is a continuation of U.S. patent application Ser. No. 10/193,076, filed Jul. 10, 2002, now U.S. Pat. No.: 6,825,235, Issued: Nov. 30, 2004, which claims the benefit of U.S. Provisional Application No. 60/304,318, filed Jul. 10, 2001. The entire teachings of these two applications are incorporated herein by reference.

BACKGROUND OF THE INVENTION

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

One serious limitation of combination chemotherapy is that anti-cancer agents generally have severe side effects, even when administered individually. For example, the well known anti-cancer agent taxol causes neutroperia, neuropathy, mucositis, anemia, thrombocytopenia, bradycardia, diarrhea and nausea. Unfortunately, the toxicity of anti-cancer agents is generally additive when the drugs are administered in combination. As result, certain types of anti-cancer drugs are generally not combined. The combined toxic side-effects of those anti-cancer drugs that are administered simultaneously can place severe limitations on the quantities that can be used in combination. Often, it is not possible to use enough of the combination therapy to achieve the desired synergistic effects. Therefore, there is an urgent need for agents which can enhance the desirable tumor attacking properties of anti-cancer agents without further increasing their undesirable side-effects, and methods for synthesizing such agents.

SUMMARY OF THE INVENTION

It has been reported in the co-pending U.S. Provisional Applications entitled TAXOL ENHANCER COMPOUNDS, filed Jul. 10, 2001, (Application No. 60/304,252), TAXOL ENHANCER COMPOUNDS, filed Mar. 6, 2002 (Application No. 60/361,946) and TAXOL ENHANCER COMPOUNDS, filed Mar. 6,2002 (Application No. 60/361,936) that certain bis[thio-hydrazide amide] compounds significantly enhance the anti-cancer activity of taxol and analogs of taxol. The entire teachings of these applications are incorporated herein by reference. Disclosed herein are methods of preparing these taxol enhancing compounds.

One embodiment of the present invention is a method of preparing a thiohydrazide product compound from a hydrazide starting compound. The hydrazide starting compound is represented by Structural Formula (I):

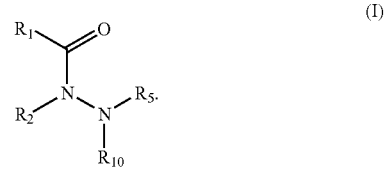

The thiohydrazide product compound is represented by Structural Formula (II):

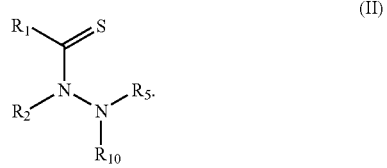

In Structural Formulas (I)-(II), $R_1$ and $R_2$ are independently an aliphatic group, a substituted aliphatic group, an aryl group or a substituted aryl group, or $R_1$ and $R_2$, taken together with the carbon and nitrogen atoms to which they are bonded, form a non-aromatic heterocyclic ring optionally fused to an aromatic ring. When $R_2$ is an aryl group or a substituted aryl group, then $R_5$ is a hydrazine protecting group; and when $R_2$ is an aliphatic or substituted aliphatic group, then $R_5$ is —H or a hydrazine protecting group. $R_{10}$ is —H or a substituted or unsubstituted alkyl group (preferably —H or an unsubstituted alkyl group, more preferably —H or methyl). The method comprises the step of reacting the starting compound with a thionylating reagent.

Another embodiment of the present invention is a method of preparing a product compound represented by Structural Formula (III):

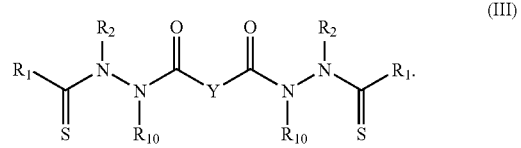

The method comprises the step of reacting Z-C(O)—Y—(CO)-Z or HO—C(O)—Y—(CO)—OH and a carboxylic acid activating agent with the thiohydrazide represented by Structural Formula (II), wherein $R_5$ is —H.

$R_1$, $R_2$ and $R_{10}$ in Structural Formula (III) are as described for Structural Formulas (I)-(II).

Y is a covalent bond or a substituted or unsubstituted straight chained hydrocarbyl group. Preferably, Y is a covalent bond, —C($R_7R_8$)—, —CH$_2$CH$_2$-, trans-(CH=CH)—, cis-(CH=CH)—, —(CC)— or a 1,4-phenylene group. More preferably, Y is a covalent bond or —C($R_7R_8$)—.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2-C6 substituted or unsubstituted alkylene group.

Each Z is a leaving group.

Another embodiment of the present invention is a method of preparing a product compound represented by Structural Formula (III) from a hydrazide starting compound represented by Structural Formula (I). The hydrazide starting compound is thionylated to form a thiohydrazide represented by Structural Formula (II), as described above. If $R_5$ is —H, then Z-C(O)—Y—(CO)-Z or HO—C(O)—Y—(CO)—OH and a carboxylic acid activating agent is reacted with the thiohydrazide represented by Structural Formula (II) to form the product compound represented by Structural Formula (III), as described above. If $R_5$ is a hydrazine protecting group, the hydrazine protecting group is first removed before reacting with Z-C(O)—Y—(CO)-Z. Z and Y are as described above.

DETAILED DESCRIPTION OF THE INVENTION

The methods disclosed herein can also be used to prepare bis[thio-hydrazide amide] compounds, which, as the term is used herein, refers to a compound represented by Structural Formula (I). In addition, asymmetrical bis[thio-hydrazide amide] comounds can also be prepared by suitable modifications of these procedures. The term "asymmetical bis[thio-hydrazide amide] compound" refers to a compound represented by Structural Formula (IV):

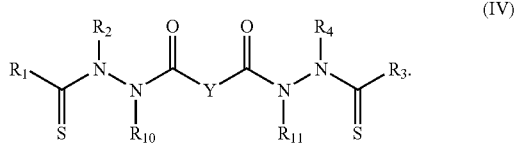

(IV)

$R_1$, $R_2$, $R_7$, $R_8$, $R_{10}$, and Y are as defined above. $R_3$ and $R_4$ are independently an aliphatic group, a substituted aliphatic group, an aryl group or a substituted aryl group, or $R_3$ and $R_4$, taken together with the carbon and nitrogen atoms to which they are bonded, form a non-aromatic heterocyclic ring optionally fused to an aromatic ring. $R_3$ and $R_4$, are independently selected from $R_1$ and $R_2$. $R_{11}$, is —H or a substituted or unsubstituted alkyl group and is selected independently of $R_8$. The method comprises a first step in which a compound represented by HOOC—Y—COOR$_6$ is amidated with a first thiohydrazide starting material represented by Structural Formula (II). $R_6$ is a carboxylic acid protecting group. The amidation forms a first intermediate represented by Structural Formula (V):

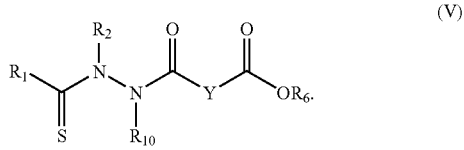

(V)

The protecting group is then removed from the carboxylic acid to form a second intermediate with a free carboxylic acid group. The second intermediate is represented by Structural Formula (VI):

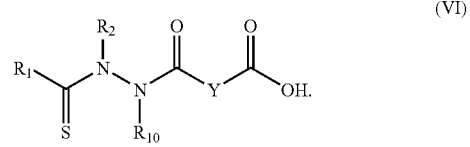

(VI)

The second intermediate is then amidated with a second thiohydrazide starting material represented by Structural Formula (II). The second thiohydrazide starting compound is typically different from the first thiohydrazide starting compound, thereby forming the asymmetical bis[thiohydrazide-amide] represented by Structural Formula (IV).

$R_1$ in Structural Formulas (I)-(VI) can be a substituted or unsubstituted aryl group (preferably a substituted or unsubstituted phenyl group). When $R_1$ can Structural Formulas (I)-(VI) is aryl or substituted aryl, $R_2$ can be a substituted or unsubstituted aliphatic group, preferably a substituted or unsubstituted lower alkyl group (e.g., methyl, ethyl, n-propyl, n-butyl or n-pentyl). Alternatively, when $R_1$, in Structural Formula (I)-(VI) is aryl or substituted aryl, $R_2$ can be a substituted or unsubstituted aryl group, preferably a substituted or unsubstituted phenyl group.

$R_1$ in Structural Formula (I)-(VI) can also be a substituted or unsubstituted aliphatic group, preferably a substituted or unsubstituted lower alkyl group (e.g., methyl, ethyl, n-propyl, n-butyl or n-pentyl). When $R_1$ in Structural Formula (I)-(VI) is a substituted or unsubstituted aliphatic group, $R_2$ can be a substituted or unsubstituted aryl group, preferably a substituted or unsubstituted phenyl group. Alternatively, when $R_1$ in Structural Formula (I)-(VI) is a substituted or unsubstituted aliphatic group, $R_2$ can also be a substituted or unsubstituted aliphatic group, preferably a substituted or unsubstituted lower alkyl group (e.g., methyl, ethyl, n-propyl, n-butyl or n-pentyl).

In another alternative, $R_2$ in Structural Formulas (I)-(VI) is an aliphatic group or a substituted aliphatic group. When $R_2$ in Structural Formulas (I)-(VI) is an aliphatic group or a substituted aliphatic group, $R_1$ is preferably a lower alkyl group or a substituted lower alkyl group.

In yet another alternative, $R_2$ in Structural Formulas (I)-(VI) is an aryl group or a substituted aryl group, more preferably a phenyl group or a substituted phenyl group.

Preferably in Structural Formulas (I)-(VI), $R_1$ is a substituted or unsubstituted aryl group, $R_2$ is methyl or ethyl, $R_7$ is —H and $R_8$ is —H or methyl. "Thionylating agent" is a reagent which, under suitable, conditions, can convert a ketone, ester or amide into a thioketone, thioester or thioamide, respectively. There are many thionylating agents known to one of ordinary skill in the art. Examples include Lawesson's Reagent, tetraphosphorus pentasulfide, Scheeren's reagent ($P_4S_{10}$—$Na_2S$), $P_4S_{10}$—N(ethyl)$_3$, Davy' Reagent and Heimgarner' reagent. Also known are conditions suitable for carrying out these conversions with thionylating agents. For example, such conditions are disclosed in Fieser and Fieser, "Reagents for Organic Synthesis", Volume 1, John Wiley & Sons, (1975) page 870-71, Fieser and Fieser, "Reagents for Organic Synthesis", Volume 5, John Wiley & Sons, (1975) page 653 and publications cited therein. Suitable conditions are also described in *Bull. Soc. Chim. Belg.* 87: 223, 229, 525 (1978), *Synthesis* 1979:941 (1979), *Tetrahedron* 35:2433 (1979) and *Tetrahedron* 21:4061 (1980). Descriptions of these reagents can also be found in Metzner and Thuillier "Sulfur Reagents in Organic Synthesis", Academic Press, 1994. The relevant portions of these publications are incorporated herein by reference.

Applicants have discovered that thionylating agents can similarly convert hydrazides to the corresponding thiohydrazide. Conditions for thionylating hydrazides are generally the same or similar to those used for thionylating ketones, esters or amides. Although some modification of those conditions may be necessary when reacting hydrazides with thionylating reagents, such modifications can readily be determined by one of ordinary skill in the art. Suitable conditions for preparing thiohydrazides from hydrazides are described in the following paragraphs.

To thionylate hydrazides, typically about one equivalent of the hydrazide is reacted with the thionylating reagent in an inert solvent. In some cases, it may be desirable to use a slight excess of thionylating reagent, for example up to about 1.5 equivalents, preferably no more than about 1.1 equivalents. Suitable inert solvents include ethereal solvents (e.g., diethyl ether, tetrhydrofuran, glyme and 1,4-dioxane), aromatic solvents (e.g., benzene and toluene) or chlorinated solvents (e.g., methylene chloride and 1,2-dichloroethane). The reaction is carried out at temperatures ranging from about room temperature to about 150° C., preferably from about 75° C. to about 125° C. Representative conditions for carrying out these reactions are found in Examples 1-9.

The term "amidating a carboxylic acid" refers to converting a carboxylic acid to an amide or a hydrazide. Many methods for converting a carboxylic acid to an amide are known in the art. Applicants have discovered that these methods can be used to prepare to the bis[thio-hydrazide amide] compounds of the present invention. Typically, the carboxylic acid is first converted into a group that is more readily displaced by an amine or hydrazine than —OH. Thus, —OH is converted into a better leaving group. A "leaving group" is a group which can readily be displaced by a nucleophile.

In one example, —OH of the carboxylic acid is converted into a better leaving group by replacing it with a halogen, typically with chloride. The carboxylic acid is thereby converted into an acid halide, e.g., an acid chloride. Reagents suitable for preparing acid chlorides from carboxylic acids are well known in the art and include thionyl chloride, oxalyl chloride, phosphorus trichloride and phosphorus pentachloride. Typically, each carboxylic acid group is reacted with about one equivalent or a slight excess of thionyl chloride, oxalyl chloride, phosphorus trichloride and phosphorus pentachloride in an inert solvent such as an ethereal solvent (e.g., diethyl ether, tetrahydrofuran or 1,4-dioxane), a halogenated solvent (e.g., methylene chloride or 1,2-dichloroethane) or aromatic solvent (e.g., benzene or toluene). When oxalyl chloride is used, a tertiary amine is often added to accelerate the reaction in quantities ranging from a catalytic amount to about one equivalent relative to oxalyl chloride.

Alternatively, the carboxylic acid is first converted into an "activated ester". An ester —COOR is said to be "activated" when —OR is readily displaced by an amine or hydrazine. —OR is more easily displaced as R becomes more electron withdrawing. Some activated esters are sufficiently stable that they can be isolated, e.g., esters wherein R is phenyl or substituted phenyl. For example, diphenylmalonate can be prepared from malonyl chloride and phenol, both commercially available from Aldrich Chemical Co., Milwaukee, Wis., by procedures described above Other activated esters are more reactive and are generally prepared and used in situ.

Formation of an activated ester in situ requires a "coupling agent", also referred to as a "carboxylic acid activating agent", which is a reagent that replaces the hydroxyl group of a carboxyl acid with a group which is susceptible to nucleophilic displacement. Examples of coupling agents include 1,1'-carbonyldiimidazole (CDI), isobutyl chloroformate, dimethylaminopropylethyl-carbodiimide (EDC), dicyclohexyl carbodiimide (DCC). When amidating by in situ generation of an activated ester, an excess of either the carboxylic acid or hydrazine can be used (typically a 50% excess, more typically about a 10-15% excess). However, it is more common when carrying out the present invention to use the hydrazine compound as the limiting reagent. Generally, from about 1.0 equivalent to about 10 equivalents of coupling agent are used relative to each carboxylic acid group, preferably from about 1.0 equivalent to about 1.5 equivalents. When DCC is used, a weak acid such as 1-hydroxybenzotriazole (HOBt) is often added to accelerate the reaction. Typically, about between one to about 1.5 equivalents of HOBt relative to DCC is used, preferably between about one to about 1.2 equivalents. The reaction is generally carried out in inert, aprotic solvents, for example, halogenated solvents such as methylene chloride, dichloroethane and chloroform, ethereal solvents such as tetrahydrofuran, 1,4-dioxane and diethyl ether and dimethylformamide. Suitable reaction temperature generally range from between about 0° to about 100°, but the reaction is preferably carried out at ambient temperature. Representative conditions for carrying out these reactions are found in Examples 1-9.

The compound represented by Structural Formula (V) comprises a carboxylic acid protecting group. Suitable protecting groups for carboxylic acids and conditions for protecting and deprotecting carboxylic acids with these groups are known in the art and are described, for example, in Greene and Wuts, "Protective Groups in Organic Synthesis", John Wiley & Sons (1991). The entire teachings of Greene and Wits are incorporated herein by reference. Specific examples of suitable carboxylic acid protecting groups for Structural Formula (V) include, but are not limited to tert-butoxy, benzoxy, phenoxy, diphenylmethoxy, triphenylmethoxy and methoxymethyl.

The compounds represented by Structural Formulas (I) and (II) can comprise a hydrazine protecting group. Amine protecting groups can also be used for protecting hydrazine groups, and conditions which are suitable for protecting and deprotecting amines with these protecting groups are also suitable for use with hydrazines. Protecting groups for amines and conditions for protecting and deprotecting amines with these protecting groups are known in the art and are disclosed, for example, in Greene and Wuts, "Protective Groups in Organic Synthesis", John Wiley & Sons (1991). Specific examples of suitable hydrazine protecting groups include, but are not limited to, tert-butoxycarbonyl (BOC), benzyloxycarbonyl (CBZ) and fluorenylmethyloxycarbonyl (FMOC).

A "straight chained hydrocarbyl group" is an alkylene group, i.e., —$(CH_2)_x$—, with one or more (preferably one) methylene groups is optionally replaced with a linkage group. x is a positive integer (e.g., between 1 and about 10), preferably between 1 and about 6, more preferably between 1 and 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine [—N($R^a$)]—, wherein $R^a$ is defined below. A preferred linkage group is —C($R_7R_8$)—, wherein $R_7$ and $R_8$ are defined above. Suitable substitutents for an alkylene group and a hydrocarbaryl group are those which do not substantially interfere with the reactions described herein. $R_7$ and $R_8$ are preferred substituents for an alkylene or hydrocarbyl group.

An aliphatic group is a straight chained, branched or cyclic (non-aromatic hydrocarbon which is completely saturated or which contains one or more units of unsaturation. Typically, a straight chained or branched aliphatic group has from one to about twenty carbon atoms, preferably from one to about ten, and a cyclic aliphatic group has from three to about eight ring carbon atoms. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with three to about eight ring carbon atoms. C1-C20 straight chained and branched alkyl groups and C3-C8 cycloalkyl groups are also referred to herein as "lower alkyl groups".

Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrrolyl, pyrazolyl, pyrazinyl, thiazole, oxazolyl and tetrazole.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl, isoindolyl, 3-isoindolyl.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

Suitable substituents on a aliphatic, aromatic non-aromatic heterocyclic or benzyl group are those which do not substantially interfere with the reactions described herein. "Interfering with a reaction" refers to substantially decreasing the yield (e.g., a decrease of greater than 50%) or causing a substantial amount of by-product formation (e.g., where by-products represent at least 50% of the theoretical yield). Interfering substituents can be used, provided that they are first converted to a protected form. Suitable protecting groups are known in the art and are disclosed, for example, in Greene and Wuts, "Protective Groups in Organic Synthesis", John Wiley & Sons (1991). Suitable substituents on an aliphatic group, non-aromatic heterocyclic group, benzylic or aryl group (carbocyclic and heteroaryl) include, for example, —OH, halogen (—Br, —Cl, —I and —F), —OR$^a$, O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CRC=CR$^a$R$^b$, —CCR$^a$, —SH, —SO$_k$R$^a$ (k is 0, 1 or 2) and —NH—C(=NH)—NH$_2$. R$^a$—R$^d$ each are independently an aliphatic, substituted aliphatic, benzyl, substituted benzyl, aromatic or substituted aromatic group, preferably an alkyl, benzylic or aryl group. In addition, —NR$^a$R$^b$, taken together, can also form a substituted or unsubstituted non-aromatic heterocyclic group. A benzylic group, non-aromatic heterocyclic group or aryl group can also have an aliphatic or substituted aliphatic group as a substituent. A substituted alkyl or aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

The term "arylene" refers to an aryl group which is connected to the remainder of the molecule by two other bonds. By way of example, the structure of a 1,4-phenylene group is shown below:

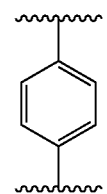

Substituents for an arylene group are as described below for an aryl group.

The present invention is illustrated by the following examples, which are not intended to be limiting in any way.

EXEMPLIFICATION

Example 1

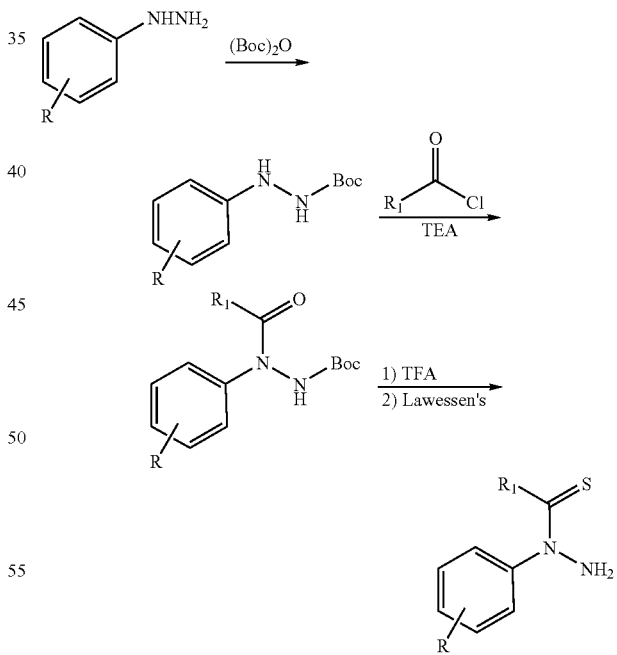

Preparation of Thiocyclohexanoic acid N-phenylhydrazide

Phenyl hydrazine (5.4 g, 50 mmol) was dissolved in dry dichloromethane (50 mL) in a 250 mL round bottom flask. Di-tert-butyl dicarbonate (10.9 g, 50 mmol) was then added with stirring at 0° C. The resultant solution was then stirred under reflux for 3 h. Removal of the volatile components under reduced pressure afforded a colorless solid, which was washed with hexane and dried in vacuo. 10 g (yield 96%) of the product was obtained as a colorless solid, which can be used in the next step without further purification. 2.5 g (12 mmol) of this material was dissolved in dry pyridine (5 mL). Cyclohexanecarbonyl chloride (2.0 mL, 15 mmol) was then added slowly at 0° C. The red solution was stirred at 0° C. for half an hour and the resultant yellow suspension was stirred at room temperature for 3 h before pouring into ice —H$_2$O (100 mL). The precipitate product was collected by filtration and washed thoroughly with H$_2$O. After one recrystallization from EtOH/H$_2$O, 3.63 g (95%) of N-Phenyl-N-Cyclohexyl-N'-tert-butoxycarbonylhydrazide was obtained as a white powder; mp 141-143° C.; $^1$H NMR (CDCl$_3$) δ 0.9-2.3 (m, 11H), 1.4 (s, 9H), 6.9 (br, 1H), 7.4 (m, 5H)ppm.

To a solution of N-Phenyl-N-Cyclohexyl-N'-tert-butoxycarbonylhydrazide (1.1 g, 3.46 mmol) in dichloromethane (6 mL) was added trifluoroacetic acid (6 mL) at 0° C. The resultant solution was stirred at 0° C. for half an hour. Volatile components were then removed under reduced pressure to afford a syrup, which was turned into a solid upon standing; this material was briefly mixed with cold 2 N NaOH (5 mL) for a few minutes at 0° C. Solid product was then collected by filtration and recrystallized from hexane to afford cyclohexanoic acid N-phenylhydrazide (0.6 g, 80% yield) as a white powder; $^1$H NMR (DMSO-d$_6$) δ 0.8-3.2 (m, 1H), 5.3 (s, 2H), 7.0-7.7 (m, 5H); ESMS calcd (C$_{13}$H$_{18}$N$_2$O ): 218.3; found: 241.1 (M+Na)$^+$.

A mixture of cyclohexanoic acid N-phenylhydrazide (0.25 g, 1.15 mmol) and Lawesson's Reagent (0.46 g, 1.15 mmol) in dry toluene (20 mL) was stirred under reflux for 1 h. After being cooled to room temperature, the mixture was filtered through a short column of silica gel (5 g) which was prewashed with benzene. Removal of benzene afforded the crude product as a solid which was purified by column chromatography on silica gel using hexane/EtOAc (4:1 v/v) as eluant. 0.15 g (60%) of thiocyclohexanoic acid N-phenylhydrazide was obtained as an off white solid. $^1$H NMR (CDCl$_3$) δ 0.8-2.4 (m, 11H), 5.65 (br, 1H), 7.1-7.6 (m, 5H); ESMS calcd (C$_{13}$H$_{18}$N$_2$S): 234.1; found: 235.1 (M+H)$^+$.

Example 2

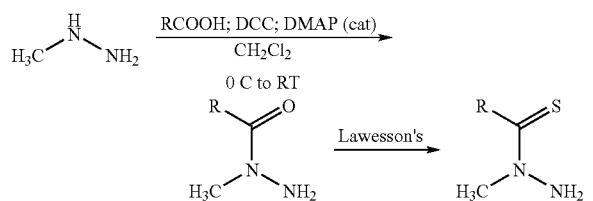

Preparation of 2.5-Dimethoxythiobenzoic acid N-methylhydrazine

DCC (4.5 g, 21.8 mmol) was added in one portion to a solution of 2,5-dimethoxybenzoic acid (3.6 g, 20 mol), methylhydrazine (1.2 ml, 23 mmol) and DMAP (30 mg, cat. ) in CH$_2$Cl$_2$ (60 ml) cooled in an ice bath. The reaction mixture was stirred overnight at room temperature. The slurry was cooled at −20° C. for 1 h and filtered. The CH$_2$Cl$_2$ solution was evaporated and the residue was dried in vacuum. The resulting crude product was dissolved in toluene (50 ml). To this solution was added Lawesson's reagent (5.8 g, 14 mmol). The mixture was refluxed for 40 min, cooled to room temperature, and directly subjected to silica gel column chromatography (eluent: 25% to 35% ethyl acetate in hexanes) to give the 2,5-dimethoxythiobenzoic acid N-methylhydrazide (3.7 g, yield: 82%) as off-white solid. $^1$H NMR (300MHz, CDCl$_3$): δ 6.88-6.80(m, 3H), 5.46 (s, 2H), 3.84(s, 3H), 3.82 (s, 3H), 3.28(s, 3H).

Example 3

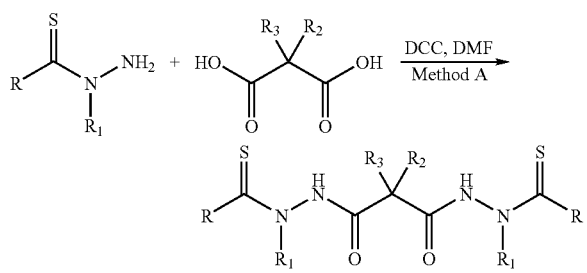

Preparation of N-Malonyl-bis[N'-methyl-N'-(thiobenzoyl) hydrazide]]

To a stirred solution of thiobenzoic acid N-methylhydrazide (0.166 g, 10 mmol), HOBt.H$_2$O (0.15 g, 11 mmol) and malonic acid (0.052 g, 5 mmol) in DMF (2 mL) was added DCC (0.22 g, 10.7 mmol) at 0° C. The resultant suspension was stirred at 0° C. for 1 h and at room temperature for 3 h. Precipitated material was filtered off and washed with EtOAc (3×15 mL). Combined filtrate and washings was washed successively with H$_2$O (2×20 mL), 5% citric acid (20 mL), H$_2$O (20 mL), Saturated NaHCO$_3$ (20 mL) and brine (20 mL). After being dried over Na$_2$SO$_4$, the solvent was removed under reduced pressure to afford the crude product as a yellow solid, which was washed with warm EtOAc. 0.16 g (yield 80%) of pure product was obtained as a yellow powder. R$_f$ 0.3 (Hexane/EtOAc 1:1 v/v); $^1$H NMR (CDCl$_3$) δ 3.1-3.8 (m, 6H), 3.4 (s, 2H), 7.1-7.45 (m, 10 H), 9.5-10.5 (m, 1H) ppm; ESMS calcd (Cl$_{19}$H$_{20}$N$_4$O$_2$S$_2$): 400.1; found: 399.1 (M–H)$^+$.

Preparation of N-(2-Methylmalonyl-bis{N'-methyl-N'-[(2.5-dimethoxy)thiobenzoyl]hydrazide]

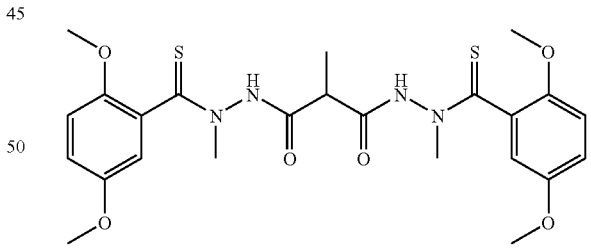

DCC (4 g, 19 mmol) was added to a solution of 2,5-dimethoxythiobenzoic acid N-methylhydrazide (3.7 g, 16.4 mmol) and 2-methylmalonic acid (2 g, 17 mmol) in DMF (20 ml) with stirring at 0° C. The reaction mixture was stirred for 1 h at room temperature. The slurry was cooled at −20° C. for 1 h and filtered. The filtrate was diluted with EtOAc (300 ml), washed with water (50 ml×3), dried with Na$_2$SO$_4$. The EtOAc solution was concentrated to minimum volume, and subjected to silica gel column chromatography (eluent: 1:4 to 2:1, ethyl acetate: hexanes) to give the title compound (3.5 g, 80%) as yellow powder. $^1$H NMR (CDCl$_3$) δ 10.12-9.14 (2H), 7.12-6.81 (m, 6H), 4.01-3.78(m, 6H), 375-3.22(m, 6H), 2.82-

2.62(m, 1H), 1.12-0.11(m, 3H); ESMS cacld ($C_{24}H_{30}N_4O_6S_2$):534.16. found: 535.1 (M+H).

Preparation of 2-Methylmalonyl-bis(2-Amino-2,3-dihydro-isoindole-1-thione)

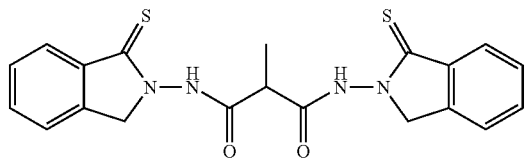

2-carboxybenzaldehyde (150 mg, 1 mmol) and carbazic acid (132 mg, 1 mmol) in 40 ml methanol was stirred at room temperature for 4 h. To this solution was added Pd/C (60 mg, containing 50% $H_2O$), the reaction was under $H_2$ atmosphere for 3 h. The reaction mixture was filtered, and the solvent was evaporated. The resulting residue was subjected to silica gel column chromatography (eluent: 20% to 50%, EtOAc in hexanes) to yield 50 mg of product. $^1$H NMR (300 MHz, $CDCl_3$): 8.71-7.45 (m, 4H), 4.78 (s, 2H), 1.61(s, 9H) The resulting product was dissolved in $CF_3COOH$ (5 ml), stirred for 30 min. The $CF_3COOH$ was evaporated, and the residue was subjected to silica gel column chromatography (eluent: 50% to 0%, hexanes in EtOAc) to give 2-amino-2,3-dihydro-isoindol-1-one (26 mg) as a white solid. $^1$H NMR (300 MHz, $CDCl_3$): 7.85-7.39 (m, 4H), 4.54 (s, 2H). MS: 149 (M+H). Subsequent Lawesson's thiolation and DCC coupling with 2-methylmaloic acid under conditions described above afforded 2-methylmalonyl-bis(2-amino-2,3-dihydro-isoindole-1-thione) as a yellow powder. $^1$HNMR ($CDCl_3$) δ 10.35 (s, 2H), 8.21-7.51(m, 8H), 5.15(s, 4H), 1.62 (s, 3H); ESMS cacld ($C_{20}H_{18}N_4O_2S_2$): 410.09; found: 411.1 (M+H).

Example 4

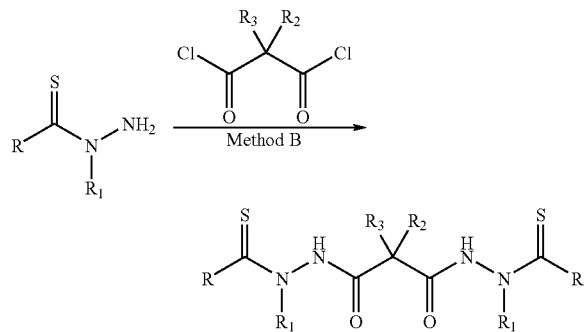

Preparation of N-Malonyl-bis[N'-methyl-N'-(thiobenzoyl) hydrazide]

To a solution of thiobenzoic acid N-methylhydrazine (10 g) stirred at 0 C were added subsequently triethylamine (8.5 mL) and malonyl dichloride (3.05 mL). The reaction mixture was stirred for 10 min, washed with water (3×50 mL), dried over sodium sulfate and concentrated. Purification by recrystallization from methylene dichloride (35 mL) gave the product as light yellow crystals (9.0 g, 75%).

Example 5

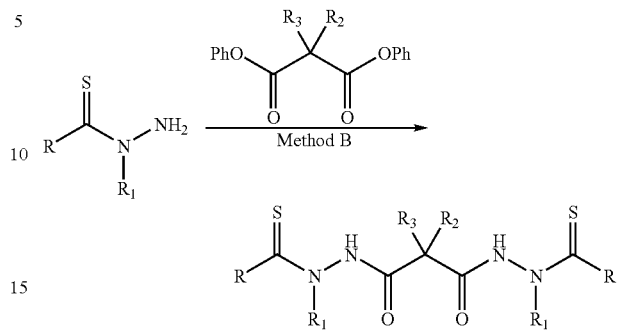

Preparation of N-Malonyl-bis[N'-methyl-N'-(thiobenzoyl) hydrazide]

A stirred solution of thiobenzoic acid N-methylhydrazide (1.66 g, 10 mmol) and diphenyl malonate (1.30 g, 5.08 mmol) in dry THF (100 mL) was heated to reflux for 72 h. Volatile components were then removed under reduced pressure. The crude product was purified by column chromatography on silica gel using a mixture of hexane and EtOAc as eluant (gradient from 4:1 v/v to 1:1 v/v). 1.07 g (51% yield) of pure product N-malonyl-bis[N'-methyl-N'-(thiobenzoyl)hydrazide] was obtained as a yellow powder. The physical properties of this compound was identical to the same product by obtained by the synthetic route described above.

Example 6

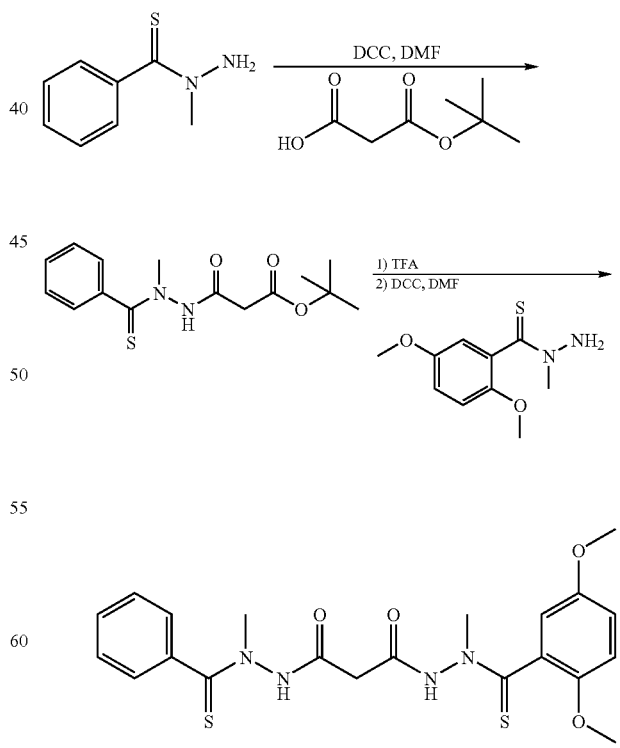

A slurry of thiobenzoic acid N-methylhydrazide (1.0 g, 6 mmol), mono-tert-butyl malonate (1.0 mL, 6 mmol), HOBt.H$_2$O (0.98 g, 7.2 mmol), and DCC (1.34 g, 6.5 mmol) in DMF (5 mL) was stirred at 0° C. for 3 h and then at room temperature for 3 h. Precipitated material was filtered off and washed with EtOAc (3×20 mL). Combined filtrate and washings was washed successively with H$_2$O (2×20 mL), 5% citric acid (20 mL), H$_2$O (20 mL), saturated NaHCO$_3$ (20 mL) and brine (20 mL). After being dried over Na$_2$SO$_4$, the solvent was removed under reduced pressure to afford the crude product as a solid, which was washed with Et$_2$O. 0.94 g (yield 51%) of pure product N'-methyl-N'-thiobenzoyl-hydrazinocarbonyl)-acetic acid tert-butyl ester was obtained as a yellow powder. $^1$H NMR (CDCl$_3$) δ 1.6-1.7 (ds, 9H), 3.1-4.1 (m, 5 H), 7.3-7.7 (m, 5H), 9.7-10.3 (ds, 1H)ppm; ESMS calcd (C$_{15}$H$_{20}$N$_2$O$_3$S): 308; found: 307 (M−H)$^+$.

A solution of N'-Methyl-N'-thiobenzoyl-hydrazinocarbonyl)-acetic acid tert-butyl ester (0.19 g, 0.6 mmol) and TFA (0.12 mL, 1.6 mmol) in dry DCM (10 mL) was stirred at 10° C.-15° C. for 12 h (reaction was monitored by TLC). Volatile components were removed under reduced pressure (bath temperature below 5° C.). After being dried in vacuo, DMF (3 mL) was added followed by the addition of DCC (0.13 g, 0.6 mmol), HOBt.H$_2$O (93 mg, 0.7 mmol) and Thio-2,5-dimethoxybenzoic acid N-methylhydrazide (0.13 g, 0.57 mmol). The resultant solution was stirred at 0° C. for half an hour and then at room temperature for 3 h. Precipitated material was filtered off and washed with EtOAc (3×10 mL). Combined filtrate and washings was washed successively with H$_2$O (2×10 mL), 5% citric acid (10 mL), H$_2$O (10 mL), Saturated NaHCO$_3$ (20 mL) and brine (20 mL). After being dried over Na$_2$SO$_4$, the solvent was removed under reduced pressure to afford the crude product as an oil, which was purified by SGC (4:1 hexane/EA to 2:1 EtOAc/Hexane). 0.14 g (yield 53%) of pure product was obtained as a yellow powder. $^1$H NMR (CDCl$_3$) δ 3.1-3.9 (m, 18H), 6.7-7.4 (m, 9H)ppm; ESMS calcd (C$_{21}$H$_{24}$N$_4$O$_4$S2): 460.1; found: 460.1 (M+H)$^+$.

Example 7

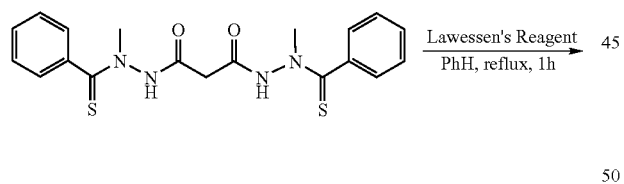

A stirred mixture of N-malonyl-bis-[N'-phenyl-N'-(thioacetyl)hydrazide) (0.1 g, 0.25 mmol) and Lawesson's reagent (0.15 g, 0.37 mmol) in dry benzene (20 mL) was heated to reflux for 1 h. After being cooled to room temperature, the mixture was filtered through a layer of silica gel, washed with THF (2×15 mL). The filtrate and washings were combined and concentrated under reduced pressure. Flush column chromatography on silica gel (hexane to 4:1 hexane/EtOAc to 2:1 hexane/EtOAc) afforded N-bisthiomalonyl-bis[N'-phenyl-N'-thioacetyl)hydrazide) as a clear syrup (16 mg, 15%). $^1$H NMR (CDCl$_3$) δ 3.80-3.95 (m, 8H), 7.02-7.30 9m, 10 H). ESMS calcd (C$_{19}$H$_{20}$N$_4$S$_4$): 432.06; found: 433.0 (M+H)$^+$.

Example 8

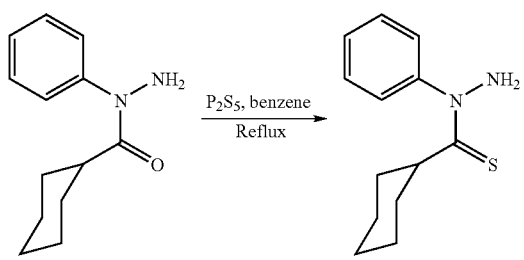

To a stirred solution of Cyclohexanoic acid N-phenylhydrazide (0.1 g, 0.45 mmol) in dry benzene (5 mL) was added P$_2$S$_5$ (0.2 g, 0.45 mol). The resultant suspension was heated to reflux for 3 h. After being cooled to room temperature, the mixture was diluted with benzene (5 mL) and was filtered through a short column of silica gel (2 g), washed with benzene and 2:1 hexane/EtOAc (15 mL each). The filtrate and washings were combined and concentrated to afford a solid. Crystallized from hexane to provide the intermediate thiocyclohexanoic acid N-phenylhydrazide as an off white solid; $^1$H NMR (CDCl$_3$) δ 0.8-2.4 (m, 11H), 5.65 (br, 1H), 7.1-7.6 (m, 5H); ESMS calcd (C$_3$H$_{18}$N$_2$S): 234.1; found: 235.1 (M+H)$^+$.

Example 9

The compounds shown below were prepared by the procedures described above. Analytical data is provided for these compounds.

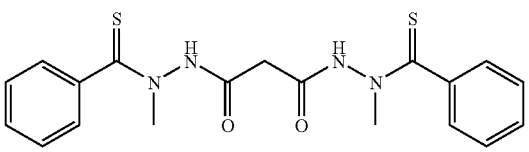

$^1$H NMR (CDCl$_3$) δ 3.1-3.8 (m, 6H), 3.4 (s, 2H), 7.1-7.45 (m, 10 H), 9.5-10.5 (m, 1H) ppm; ESMS calcd (C$_{19}$H$_{20}$N$_4$O$_2$S$_2$): 400.1; found: 399.1 (M−H)$^+$.

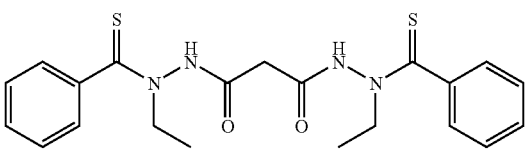

¹H NMR (CDCl₃) δ 1.0-1.35 (m, 6H), 3.0-4.3 (m, 6H), 7.05-7.40 (m, 10H), 9.1-10.1 (m, 2H); ESMS cacld (C₁₂H₂₄N₄O₂S₂): 428.8; found: 427 (M–H)+. Anal Calc For C₂₁, H₂₄N₄O₂S₂(428.13) C, 58.85; H, 5.64; N, 13.07; S, 14.96. Found: C, 58.73; H, 5.62; N, 12.97; S, 14.96.

¹H NMR (CDCl₃) δ 0.5 (t, 3H, J=7), 1.1-1.6 (m, 2H), 2.7 (t, 1H, J=7), 3.1-3.3 (m, 6H), 7.0-7.3 (m, 10H), 10.25 (s, 2H) ppm; MS (C₂₁H₂₄N₄O₂S₂): 428.1; found: 427.1 (M–H)⁺.

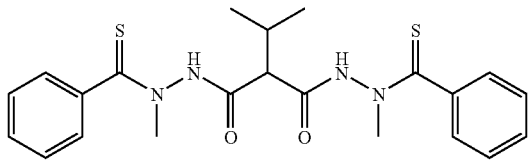

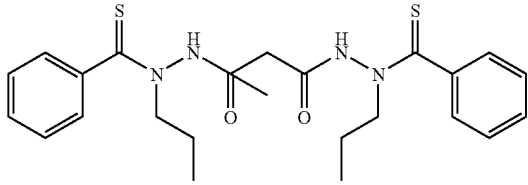

¹H NMR (CDCl₃) δ 0.5 (d, 6H, J=7), 0.9-1.2 (m, 1H), 3.0-41 (m, 7H), 7.1-7.4 (m, 10H), 10.3 (s, 2H)ppm; ESMS (C₂₂H₂₆N₄O₂S₂): 442.1; found: 441.1 (M–H)⁺.

¹H NMR (CDCl₃) δ 0.7-1.0 (m, 6H), 1.4-1.9 (m, 4H), 3.1-4.2 (m, 6H), 7.1-7.4 (m, 10H), 8.9-10.2 (m, 2H) ppm; ESMS (C₂₃H₂₈N₄O₂S₂): 456.1; found: 455.1 (M–H)⁺.

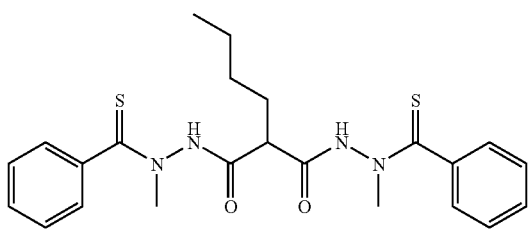

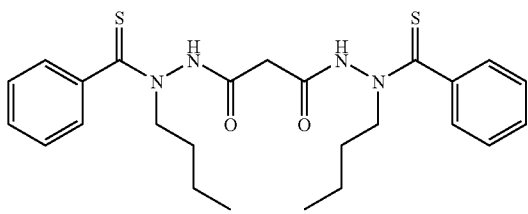

¹H NMR (CDCl₃) δ 0.4-1.3 (m, 5H), 1.5-1.8 (m, 2H), 3.0-3.7 (m, 6H), 7.1-7.5 (m, 10H), 11 (s, 2H)ppm; MS (C₂₃H₂₈N₄O₂S₂): 456.1; found: 455.1 (M–H)⁺.

mp 141-143° C.; ¹H NMR (CDCl₃) δ 0.6-1.05 (m, 6H), 1.1-1.9 (m, 8H), 3.0-4.2 (m, 6H), 7.0-7.35 (m, 10H), 8.9-11 (ms, 2H). ESMS (C₂₅H₃₂N₄O₂S₂): 484.2; found: 483.1 (M–H)⁺. Anal Calc For C₂₅H₃₂N₄O₂S₂ (484.2) C, 61.95; H, 6.65; N, 11.56; S, 13.23. Found: C. 61.98; H, 6.52; N, 11.26; S, 13.16.

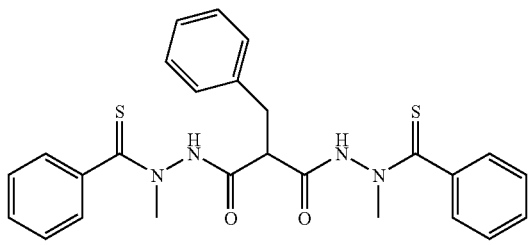

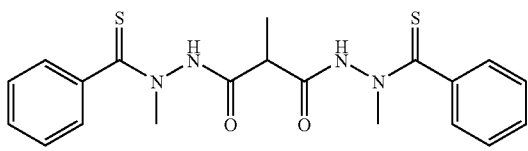

¹H NMR (CDCl₃) δ 2.1 (d, 2H, J=7), 2.9 (t, 1H, J=7), 3.1-3.5 (m, 6H), 6.8-7.4 (m, 15 H), 11 (s, 2H)ppm; MS (C₂₆H₂₆N₄O₂S₂): 490.1; found: 489.1 (M–H)⁺.

¹H NMR (DMSO-d₆) δ 0.4-0.9 (dd, 3H, J=7), 2.7 (q, 1H), 3.1-3.6 (m, 6H), 7.1-7.5 (m, 10H), 10.9 (br, 2H)ppm; ESMS (C₂₀H₂₂N₄O₂S₂): 414; found: 413 (M–H)⁺.

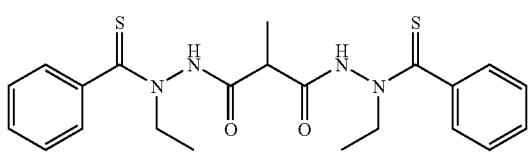

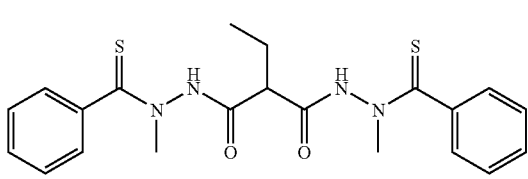

¹H NMR (CDCl₃) δ 0.4 (d, 3H, J=7), 1.0-1.4 (m, 6H), 2.75 (q, 1H), 3.0-4.3 (m, 4H), 7.1-7.4 (m, 10H), 10.6 (s, 2H); ESMS Calc For (C₂₂H₂₆N₄O₂S₂): 442.1; found: 441

(M–H)+. Anal Calc For $C_{22}H_{26}N_4O_2S_2$ (442.15) C, 59.70; H, 5.92; N, 12.66; S, 14.49. Found: C 59.64; H, 5.92; N, 12.59; S, 14.47.

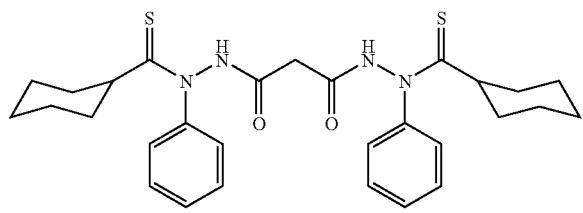

$^1$H NMR (DMSO-$d_6$) δ 0.9-1.8m, 22H), 3.1-3.5 (m, 2H), 7.2-7.6 (m, 10H), 11.1-11.7 (ms, 2H) ppm; ESMS calcd ($C_{29}H_{36}N_4O_2S_2$):536.3; found: 537.3(M–H)+.

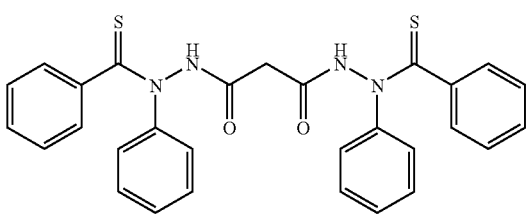

$^1$H NMR (DMSO-$d_6$) δ 3.20 (br, 2H), 7.1-7.6 (m, 20 H), 11.5 (s, 2H)ppm; ESMS calcd (C29H24N4O2S2): 524.1; found: 523.1 (M–H)+.

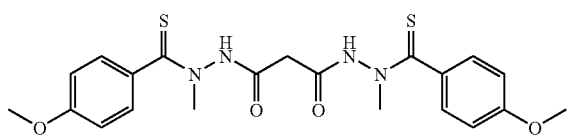

$^1$H NMR (CDCl$_3$) δ 3.0-4.3 (m, 14H), 6.6-7.5 (m, 8H), 10.4 (s, 2H) ppm; ESMS calcd ($C_{21}H_{24}N_4O_2S_2$): 460.2; found: 461.2 (M+H)+.

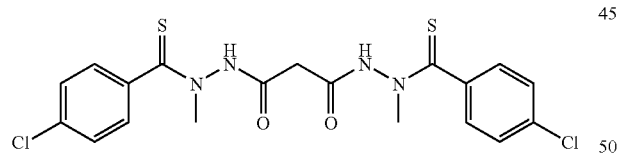

$^1$H NMR (CDCl$_3$) δ 2.65-3.60 (m, 8H), 7.2-7.4 (m, 8H), 11.1 (br, 2H); ESMS calcd ($C_{19}H_{18}Cl_2N_4O_2S_2$): 468.0; found: 467.9 (M–H)+.

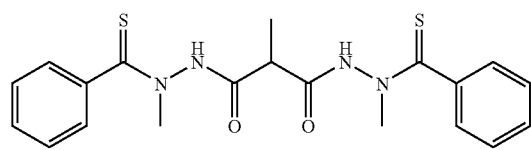

$^1$H NMR (CDCl$_3$) δ 0.4 (d, 3H, J=7), 2.7 (q, 1H, J=7), 3.0-3.8 (m, 6H) 7.2-8.2 (m, 8H), 10.5-10.7 (ms, 2H) ppm; ESMS calcd ($C_{20}H_{20}Cl_2N_4O_2S_2$): 482.0; found: 481.0 (M–H)+.

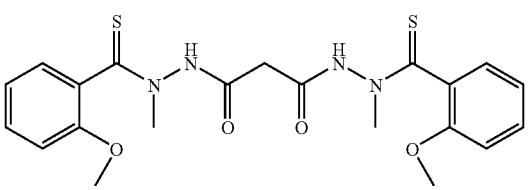

$^1$H NMR (CDCl$_3$) δ 2.9-3.8 (m, 6H), 7.3-7.7 (m, 4H), 8.0-8.3 (m, 4H), 10.9 (s, 2H); ESMS calcd ($C_{10}H_{18}N_6O_6S_2$): 490.0; found: 489.0 (M–H)+.

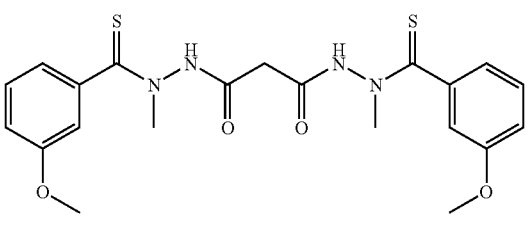

$^1$H NMR (CDCl$_3$) δ 3.1-3.9 (m, 14H), 6.7-7.8 (m, 8H), 9.0-10 (m, 2H) ppm; ESMS calcd ($C_{21}H_{24}N_4O_4S_2$): 460.1; found: 459.1 (M–H)+.

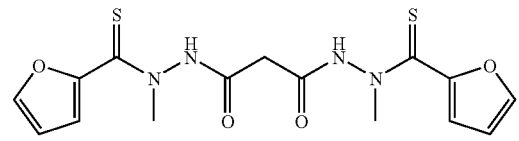

(SBR-11-5032): $^1$H NMR (CDCl$_3$) δ 3.0-3.9 (m, 14H), 6.7-7.3 (m, 8H), 9.0-10 (m, 2H) ppm; ESMS calcd ($C_{21}H_{24}N_4O_4S_2$): 460.1; found: 459.1 (M–H)+.

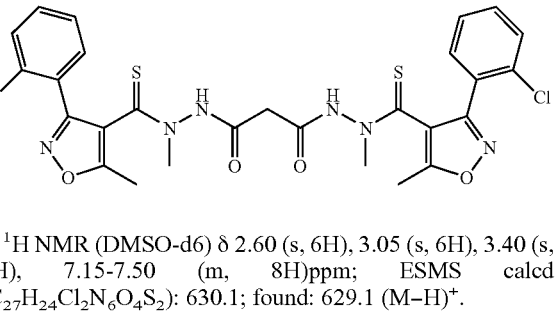

$^1$H NMR (acetone-$d_6$) δ 3.5 (s, 2H), 6.45 (d, 2H, J=5), 6.9 (d, 2H, J=5), 7.2-7.6 (m, 12H), 10.6 (s, 2H) ppm; ESMS calcd ($C_{25}H_{20}N_4O_4S_2$): 504.1; found: 503.1 (M–H)+.

$^1$H NMR (DMSO-d6) δ 2.60 (s, 6H), 3.05 (s, 6H), 3.40 (s, 2H), 7.15-7.50 (m, 8H)ppm; ESMS calcd ($C_{27}H_{24}Cl_2N_6O_4S_2$): 630.1; found: 629.1 (M–H)+.

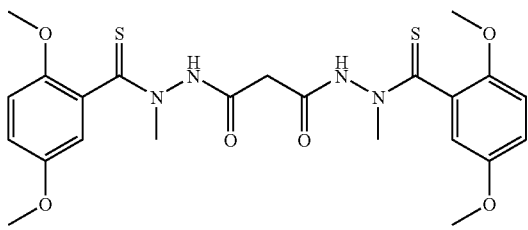

$^1$H NMR (CDCl$_3$) δ 10.06-8.82 (2H), 7.16-6.81(m,6H), 4.01-3.81(m, 6H), 3.78-3.11 (m,6H), 2.81-2.58(m,2H): ESMS cacld (C$_{23}$H$_{28}$N$_4$O$_6$S$_2$): 520.15; found: 521 (M+H).

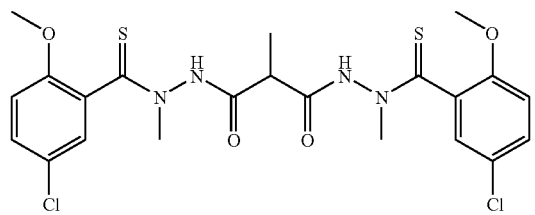

$^1$H NMR (CDCl$_3$) δ 10.21-9.02(2H), 7.60-6.81 (m, 6H), 4.14-3.88(m, 6H) 3.87-3.18 (m,6H), 2.84-2.65(m, 1H),1.10-0.16 (m, 3H); ESMS cacld (C$_{22}$H$_{24}$Cl$_2$N$_4$O$_4$S$_2$): 542.06; found: 543(M+H).

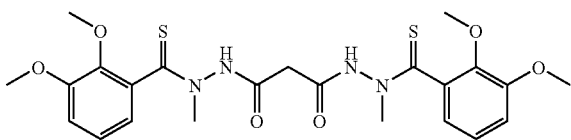

$^1$H NMR (CDCl$_3$) δ 10.38-9.01 (2H), 7.12-6.82 (m, 6H), 3.92-3.78(m, 12H), 3.75-3.06(m, 6H), 2.61-2.51 (m, 2H); ESMS cacld (C$_{23}$H$_{28}$N$_4$O$_6$S$_2$): 520.15; found: 521 (M+H).

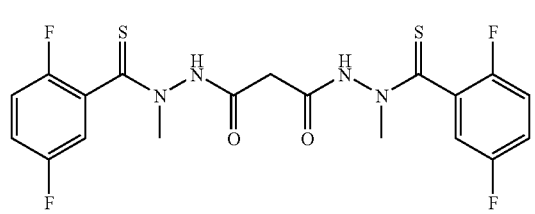

$^1$H NMR (CDCl$_3$) δ 10.02-9.20 (2H), 7.63-7.01 (m, 6H), 4.21-3.22(m, 6H), 1.88-1.36 (m, 2H); ESMS cacld (C$_{19}$H$_{16}$F$_4$N$_4$O$_2$S$_2$): 472.07; found: 473 (M+H).

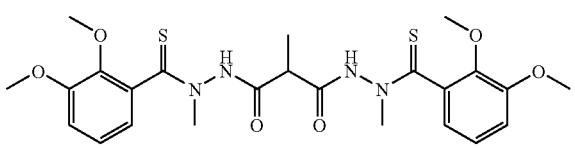

$^1$H NMR (CDCl$_3$) δ 9.45-8.63 (2H), 7.18-6.81 (m, 6H), 4.01-3.80(m, 6H), 3.78-3.24 (m, 6H), 2.62-2.50(m, 1H), 1.74-0.11 (m, 3H); ESMS cacld (C$_{24}$H$_{30}$N$_4$O$_6$S$_2$):534.16; found: 535 (M+H).

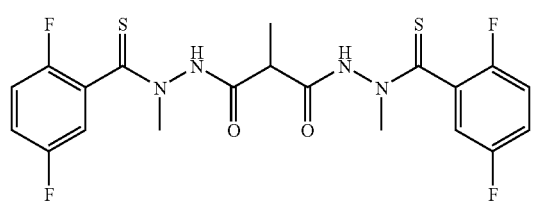

$^1$H NMR (CDCl$_3$) δ 7.93-7.61 (2H), 7.40-6.92 (m, 6H), 3.98-3.41 (m, 6H), 2.19-0.93 (m, 4H); ESMS cacld (C$_{20}$H$_{18}$F$_4$N$_4$O$_2$S$_2$): 486.08; found: 487 (M+H).

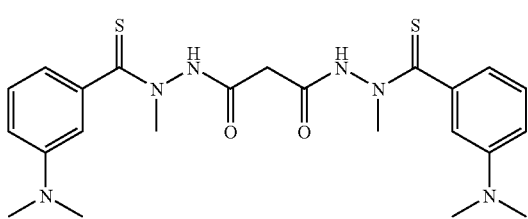

$^1$H NMR (CDCl$_3$) δ 10.19-8.61 (2H), 7.26-6.52(m, 6H), 3.81-3.08(m, 8H), 3.01-2.88(m, 12H). ESMS cacld (C$_{23}$H$_{30}$N$_6$O$_2$S$_2$): 486.19; found: 487 (M+H).

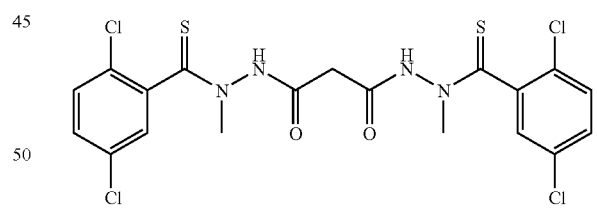

$^1$H NMR (CDCl$_3$) δ 10.12-9.21(2H), 7.67-7.23 (m, 6H), 3.94-3.22 (m, 6H), 2.01-1.21 (m, 2H); ESMS cacld (C$_{19}$H$_{16}$Cl$_4$N$_4$O$_2$S$_2$): 535.95; found: 537(M+H).

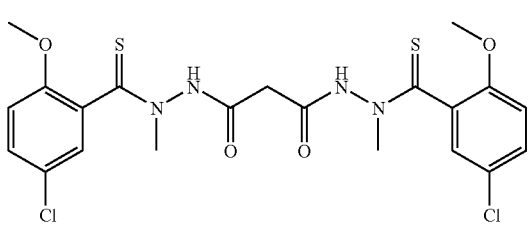

$^1$H NMR (CDCl$_3$) δ 9.92-8.80 (2H), 7.41-6.72 (m, 6H), 4.01-3.81(m,6H), 3.80-3.15 (m,6H), 2.76-2.42(m, 2H); ESMS cacld (C$_{2}$H$_{22}$Cl$_2$N$_4$O$_4$S$_2$):528.05; found: 529(M+H).

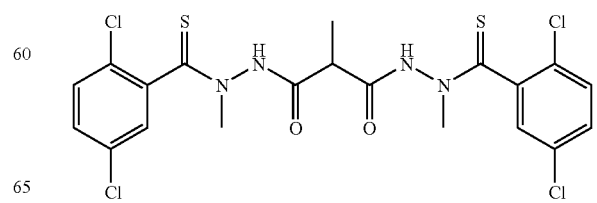

¹H NMR (CDCl₃) δ 7.78-7.23 (2H), 4.56-3.10 (m, 6H), 2.34-1.12 (m, 4H); ESMS cacld (C₂₀H₁₈Cl₄N₄O₂S₂): 549.96; found: 551 (M+H).

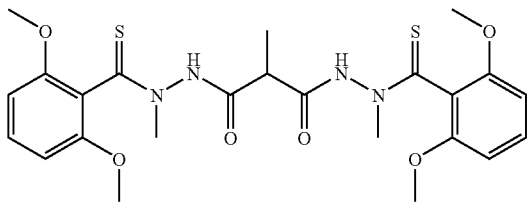

¹H NMR (CDCl₃) δ 9.92-9.01 (2H), 7.38-7.15 (m,3H), 6.66-6.51 (m,3H), 3.98-3.75 (m,12H), 3.72-3.21(m,6H), 2.01-0.42 (m, 4H); ESMS cacld (C₂₄H₃₀N₄O₆S₂):534.16; found: 535 (M+H).

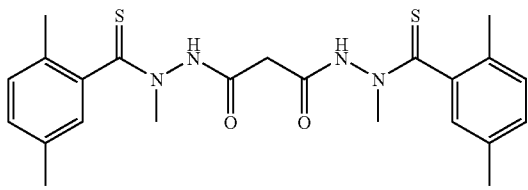

¹H NMR (CDCl₃) δ 10.51-9.82 (2H), 7.42-6.80 (m, 6H), 3.92-3.04(m, 6H), 2.60-1.21 (m, 14H); ESMS cacld (C₂₃H₂₈N₄O₂S₂): 456.17; found: 457(M+H).

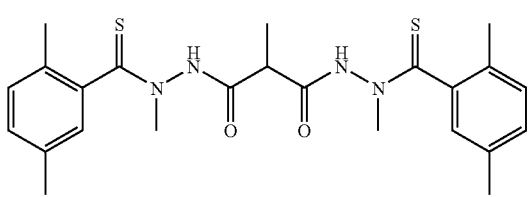

¹H NMR (CDCl₃) δ 10.51-8.82 (2H), 7.11-6.89 (m, 6H), 3.81-3.02 (m, 6H), 2.40-1.02 (m, 16H); ESMS cacld (C₂₄H₃₀N₄O₂S₂): 470.18; found: 471(M+H).

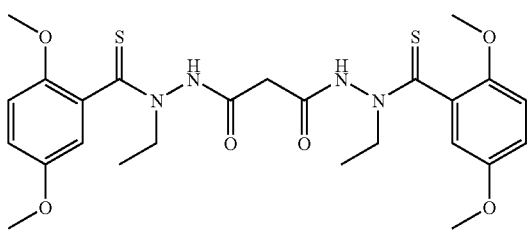

¹H NMR (CDCl₃) δ 9.86-8.42 (2H), 7.01-6.6 (m, 6H), 4.18-3.51 (m, 16H), 3.22-2.26 (2H), 1.40-1.04 (m, 6H); ESMS cacld (C₂₅H₃₂N₄O₆S₂):548.18; found: 547 (M−H).

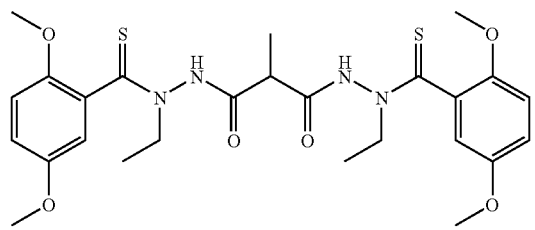

¹H NMR CDCl₃) δ 9.99-8.41 (2H), 7.01-6.68 (m, 6H), 4.18-3.56 (m, 16H), 1.40-0.02 (m, 10H ); ESMS calcd (C₂₆H₃₄N₄O₆S₂): 562.19; found: 561(M−H).

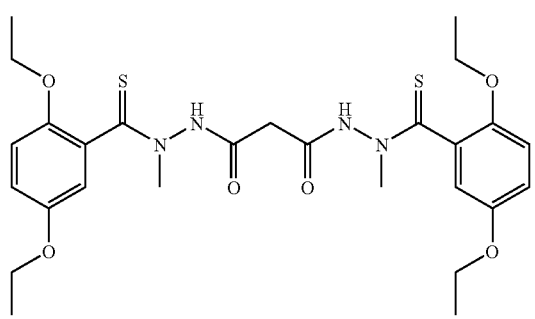

¹H NMR (CDCl₃) δ 10.12-8.82 (2H), b7.03-6.62 (m, 6H), 4.21-3.87 (m, 8H), 3.84-3.01(m, 6H), 2.71-2.42 (m, 2H), 1.56-1.21 (m, 12H); ESMS cacld (C₂₇H₃₆N₄O₆S₂): 576.21; found: 5.77(M+H).

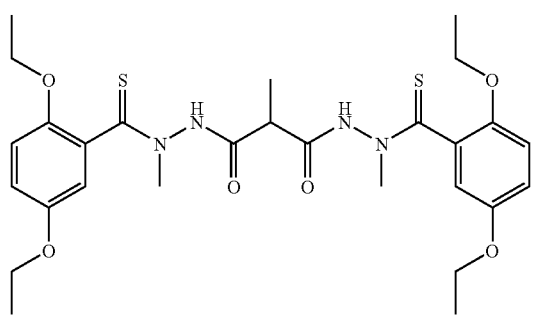

¹H NMR (CDCl₃) δ 69.81-8.79 (2H), 7.01-6.64 (m, 6H), 4.21-3.81(m, 8H), 3.80-3.22 (m, 6H), 1.54-1.20 (m, 13H), 1.01-0.16 (m, 3H); ESMS cacld (C₂₈H₃₈N₄O₆S₂): 590.22; found: 591 (M+H).

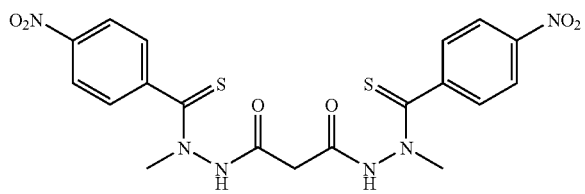

¹H NMR (DMSO-d₆): δ 8.25 (d, J=8.1 Hz, 4H), 7.50 (d, J=8.1 Hz, 4H), 3.7-3.3 (m, 8H); ESMS cacld for C₁₉H₁₈N₆O₆S₂: 490.1. Found: 489.0 (M−H).

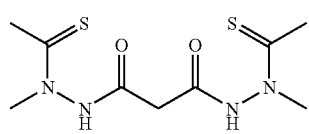

¹H NMR (CDCl₃): δ 3.6-3.4 (m, 8H), 2.7-2.5 (m, 6H); ESMS cacld for C₉H₁₆N₄O₂S₂: 276.1. Found: 274.9 (M−H).

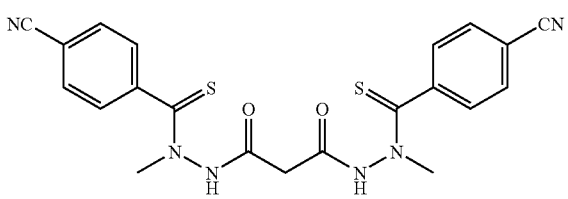

¹H NMR (CDCl₃): δ 10.25 (m, 2H), 7.7-7.4 (m, 8H), 3.7 (m, 2H), 3.35 (m, 6H); ESMS calcd for C₂₁H₁₈N₆O₂S₂: 450.1. Found: 449.0 (M−H).

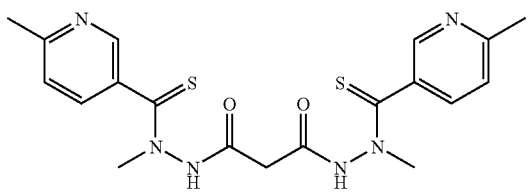

¹H NMR (CDCl₃): δ 8.2 (s, 2H), 7.7-7.5 (m, 4H), 3.7-3.4 (m, 8H), 2.9-2.8 (m, 6H); ESMS cacld for C₁₉H₂₂N₆O₂S₂: 430.1. Found: 431.1 (M+H).

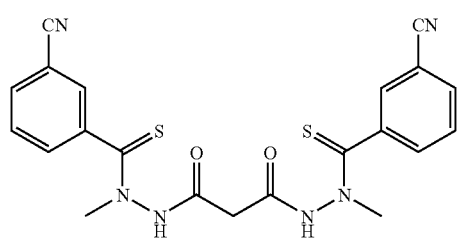

¹H NMR (CDCl₃): δ 10.0-9.2 (m, 2H), 7.9-7.45 (m, 8H), 4.0-3.4 (m, 8H); ESMS calcd for C₂₁H₁₈N₆O₂S₂: 450.1. Found: 451.0 (M+H).

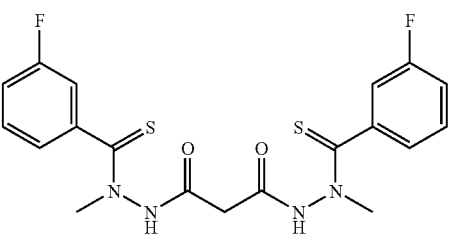

¹H NMR (CDCl₃): δ 10.1-9.4 (2H), 7.5-7.2 (m, 8H), 3.9-3.3 (m, 8H); ESMS cacld for C₁₉H₁₈F₂N₄O₂S₂: 436.1. Found: 437.1 (M+H).

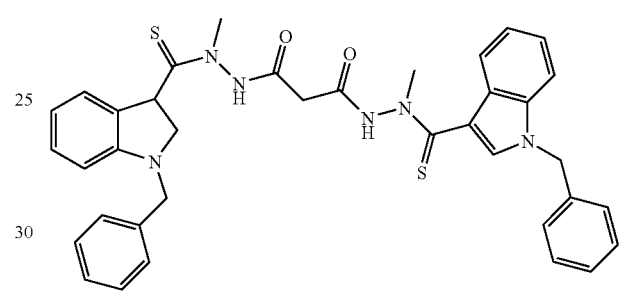

¹H NMR (CDCl₃): δ 3.3 (s, 2H), 3.6 (s, 6H), 5.25 (s, 4H), 7.05-7.3 (m, 16H), 7.6 (s, 2H), 7.9 (d, 2H, J=6), 10.56 (s, 2H)ppm; ESMS calcd (C₃₇H₃₄N₆O₂S₂): 658.2; found: 659.2 (M+H)⁺.

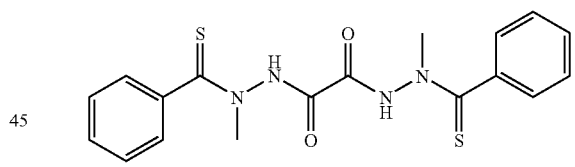

¹H NMR (DMSO) δ 11.98 (2H), 7.44-7.12 (m, 10H), 3.69-3.14(s, 6H). ESMS cacld (C₁₈H₁₈N₄O₂S₂): 386.09; found: 387.1 (M+H).

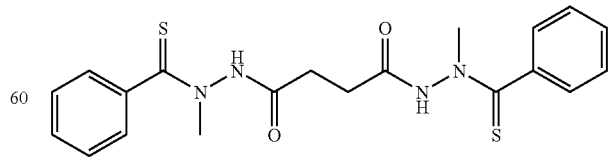

¹H NMR (CHCl₃) δ 69.48-8.55 (2H), 7.56-7.20(m, 10H), 3.80-3.31(m, 6H), 2.88-2.22(m, 4H). ESMS cacld (C₂₀H₂₂N₄O₂S₂): 414.12; found: 415.1 (M+H).

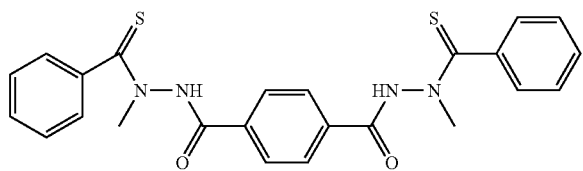

¹H NMR (300 MHz, CDCl₃) δ 10.21-9.91 (m, 2H), 8.06-7.32 (m, 14H), 3.91-3.56 (m, 6H). ESMS cacld (C$_{24}$H$_{22}$N$_4$O$_2$S$_2$): 462.12; found: 463 (M+H).

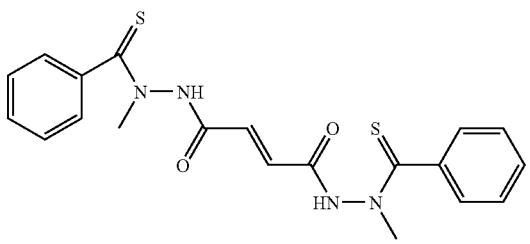

¹H NMR (300 MHz, DMSO-d$_6$) δ 11.60-11.40 (m, 2H), 7.48-6.46(m, 12H), 3.64-3.3.30(m, 6H). ESMS cacld (C$_{20}$H$_{20}$N$_4$O$_2$S$_2$): 412.10; found: 413 (M+H).

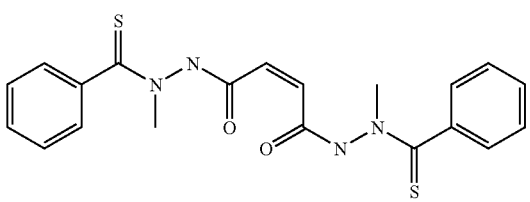

¹H NMR (300 MHz, CDCl₃) δ 7.58-7.20(m, 12H), 3.68-3.20(m, 6H). ESMS cacld (C$_{20}$H$_{20}$N$_4$O$_2$S$_2$): 412.10; found: 413 (M+H).

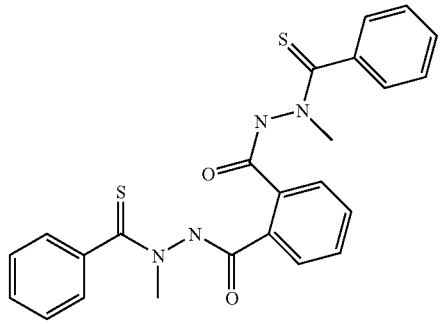

¹H NMR (300 MHz, CDCl₃) δ 9.65-8.70 (2H), 8.01-7.21 (m, 14H), 3.84-3.40(m, 6H). ESMS cacld (C$_{24}$H$_{22}$N$_4$O$_2$S$_2$): 462.12; found: 463 (M+H).

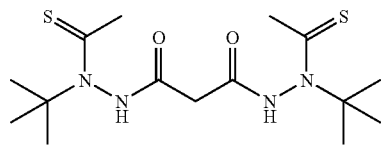

¹H NMR (CDCl₃): δ 2.63 (s, 2H); 2.18 (s, 6H); 1.25 (s, 18H). MS calcd for C$_{15}$H$_{28}$N$_4$O$_2$S$_2$: 360.2. Found: 383.1 (M+Na).

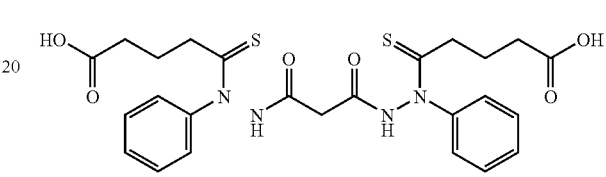

¹H NMR (CDCl₃): δ 7.3 (m, 10H); 3.2 (m, 2H); 2.45 (t, J=7.4 Hz, 4H); 2.21 (t, J=7.4 Hz, 4H); 1.90 (m, 8H). MS calcd for C$_{25}$H$_{28}$N$_4$O$_6$S$_2$: 544.15. Found: 567.2 (M+Na).

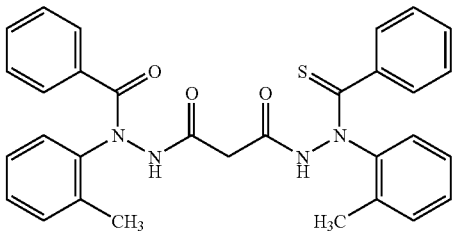

¹H NMR (CDCl₃): δ 7.4-1 (m, 18H); 3.3 (br s, 2H); 2.5 (br s, 6H). MS calcd for C$_{31}$H$_{28}$N$_4$O$_3$S: 536.2. Found: 537.2 (M+H).

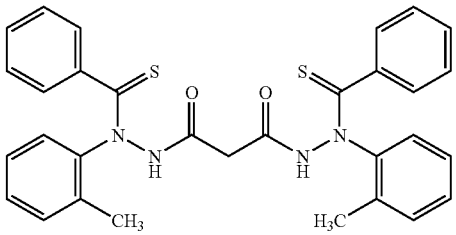

¹H NMR (CDCl₃): δ 7.2 (m, 18H); 3.5 (br s, 2H); 2.4 (br s, 6H). MS calcd for C$_{31}$H$_{28}$N$_4$O$_2$S$_2$: 552.2. Found: 553.2 (M+H).

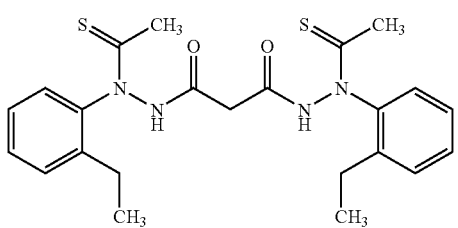

¹H NMR (CDCl₃): δ 7.8-7.4 (br s, 8H), 3.75-3.5 (m, 2H), 3.95-3.8(m, 4H), 2.58 (s, 6H), 1.4 (m, 6H). ESMS cacld for C₂₃H₂₈N₄O₂S₂: 456.2. Found: 479.2 (M+Na).

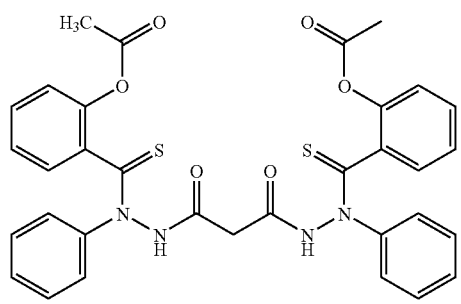

¹H NMR (CDCl₃): δ 7.5 (br s, 18H), 3.4 (br s, 2H), 2.45 (s, 6H). ESMS cacld for C₃₃H₂₈N₄O₆S₂: 640.1. Found 641.1 (M+H).

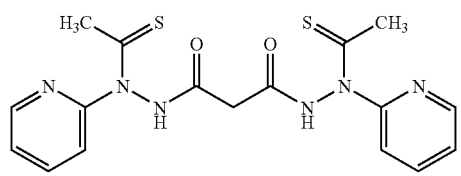

¹H NMR (CDCl₃): δ 8.3-8.05 (m, 4H), 7.75 (t, J=8.0 Hz, 2H), 7.1 (br s, 2H), 3.74 (s, 2H), 2.38 (s, 6H). ESMS cacld for C₁₇H₁₈N₆S₂: 402.1. Found: 403.1 (M+H).

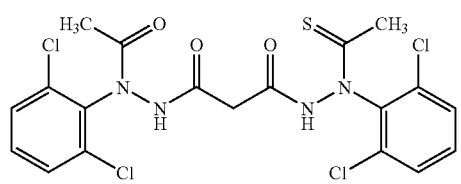

¹H NMR (CDCl₃): δ 7.7-7.2 (m, 6H), 3.2 (s, 2H), 2.58 (s, 3H), 2.15 (s, 3H). ESMS calcd for C₁₉H₁₆Cl₄N₄O₃S: 519.9. Found: 520.9 (M+H).

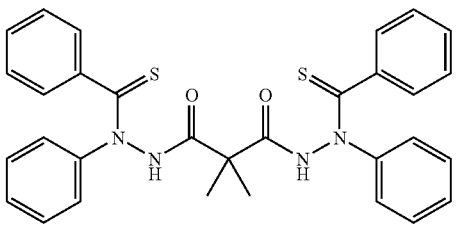

¹H NMR (CDCl₃-D₂O): δ 7.45-7.15 (m, 20 H), 1.6 (br s, 6H). ESMS cacld for C₃₁, H₂₈N₄O₂S₂: 552.2. Found: 553.2 (M+H).

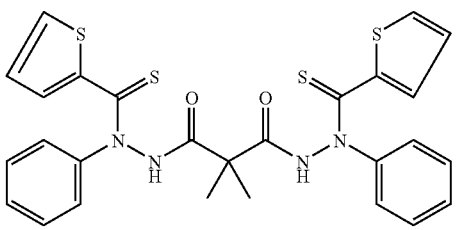

¹H NMR (DMSO-d₆): δ 11.3 (s, 2H), 7.75 (d, J=6.0 Hz, 2H), 7.5-7.4 (m, 12 H); 6.9 (m, 2H); ESMS cacld for C₂₇H₂₄N₄O₂S₄: 564.1. Found: 565.2 (M+H).

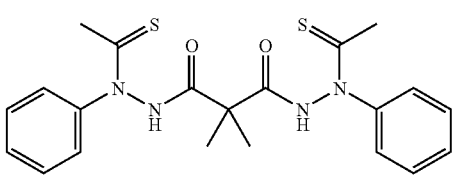

¹H NMR (CDCl₃): δ 7.38 (m, 10 H), 2.40 (s, 6H), 1.5-1.6 (6H); ESMS cacld for C₂₁H₂₄N₄O₂S₂: 564.1. Found: 565.2 (M+H).

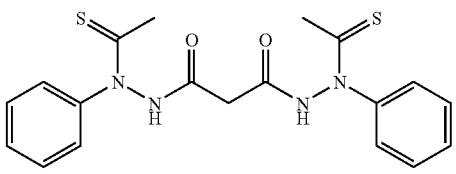

¹H NMR (DMSO-d6): δ 11.5 (m, 2H); 7.5 (m, 10H); 3.2 (m, 2H); 2.6 (s, 3H); 2.5 (s, 3H). MS calcd (400.1). Found: 423.1 (M+Na).

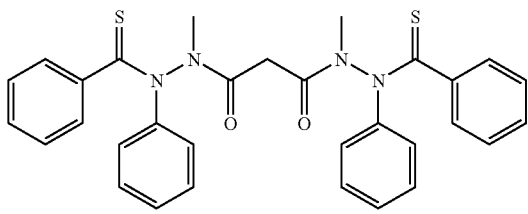

$^1$H NMR (CDCl$_3$) δ 3.3-4.5 (m, 8H), 7.1-7.8 (m, 20 H)ppm; ESMS calcd (C$_{31}$H$_{28}$N$_4$O$_2$S$_2$): 552; found: 551. (M−H)$^+$.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the structural formula:

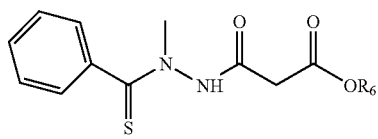

wherein R$_6$ is a carboxylic acid protecting group.

2. The compound of claim 1, wherein R$_6$ is selected from the group consisting of: tert-butyl, benzyl, phenyl, diphenylmethyl, triphenylmethyl and methoxymethyl.

3. The compound of claim 2, wherein R$_6$ is tert-butyl.

4. A method of preparing a compound represented by the following structural formula:

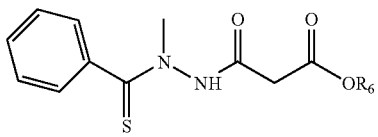

wherein R$_6$ is a carboxylic acid protecting group, comprising:
reacting thiobenzoic acid N-methylhydrazide with Z-(O)C—CH$_2$—COOR$_6$, or HO—(O)C—CH$_2$—COOR$_6$ and a carboxylic acid activating group, wherein R$_6$ is a carboxylic acid protecting group, and Z is a leaving group, thereby forming the compound.

* * * * *